United States Patent [19]

Streber

[11] Patent Number: 5,264,428
[45] Date of Patent: Nov. 23, 1993

[54] USE OF STIGMASTA-4-EN-3-ONE IN THE TREATMENT OF ANDROGEN DEPENDENT DISEASES

[75] Inventor: August S. Streber, Aichen, Fed. Rep. of Germany

[73] Assignee: Kanoldt Arzneimittel GmbH, Fed. Rep. of Germany

[21] Appl. No.: 876,131

[22] Filed: Apr. 29, 1992

Related U.S. Application Data

[63] Continuation of Ser. No. 656,783, Feb. 15, 1991, abandoned.

[30] Foreign Application Priority Data

Feb. 16, 1990 [DE] Fed. Rep. of Germany ....... 4004920

[51] Int. Cl.$^5$ .............................................. A61K 31/56
[52] U.S. Cl. ..................................................... 514/177
[58] Field of Search ......................................... 514/177

[56] References Cited

U.S. PATENT DOCUMENTS

3,647,829  3/1972  Kruger et al. ................... 260/397.4

FOREIGN PATENT DOCUMENTS

0151385  8/1985  United Kingdom .

OTHER PUBLICATIONS

Chemical Abstracts, 96(2): 11546r, 1981.
Chemical Abstracts, 99(12): 93577a, 1983.
Chemical Abstracts, 104(22): 193257m, 1986.
Chemical Abstracts, 105(18): 158615a, 1986.
Chemical Abstracts, 106(4): 23080x, 1986.

*Primary Examiner*—Frederick E. Waddell
*Assistant Examiner*—Kimberly R. Jordan
*Attorney, Agent, or Firm*—Pravel, Hewitt, Kimball & Krieger

[57] ABSTRACT

A pharmaceutical preparation which comprises stigmasta-4-en-3-one as the active ingredient. This active ingredient can be used for the treatment of androgen-dependent diseases, especially for the treatment of benign prostatic hyperplasia.

3 Claims, No Drawings

USE OF STIGMASTA-4-EN-3-ONE IN THE TREATMENT OF ANDROGEN DEPENDENT DISEASES

This is a continuation of co-pending application Ser. No. 07/656,783 filed on Feb. 15, 1991, now abandoned.

FIELD OF THE INVENTION

This invention concerns a pharmaceutical preparation as well as the use of stigmasta-4-en-3-on in human and/or veterinary medicine.

BACKGROUND OF THE INVENTION

Various illnesses, especially some malignant and benign tumors are controlled by androgenous sexual hormones. For example, benign prostatic hyperplasia is influenced, triggered or kept in growth by a reduction of the androgens and thereby by a relative increase of the estrogens. Strangury, residual urine and finally acute urinary blockage are observed as symptoms of this illness. The purpose of therapy must be to increase the micturition volume as well as the maximal urine flow quantity, and at the same time to reduce the residual amount of urine.

Such androgen-dependent tumors or neoplasms and disease are, inter alia, treated with anti-androgens. These are substances which suspend the androgenous effect at the target location. Cyproteronacetate and androsten and estran derivatives are known as anti-androgens on the market.

Anti-androgens are used therapeutically for men in the case of prostate tumors of pubertas praecox (too early commencement of puberty) and in the case of hypersexuality, ranging up to criminal sexual aggression. For women, the indications for therapy using anti-androgens are hirsutism as well as acne which is caused by androgens.

However, to some extent substantial side effects are observed. In the case of men, an inhibition of spermiogenesis is observed in up to 60% of patients, which may lead as far as sterility. In about 15% of the cases, there is inhibition of the libido and of potency. Furthermore, an increase in weight as well as a gynaecomastia are observed in from 20 to 25% of cases.

Particularly for the treatment of benign prostatic hyperplasia, plant extracts from the roots of nettles (radix urticae) are used. For example, a dry extract obtained from radix urticae having 20% carbinol is obtainable on the market for the treatment of benign prostatic hyperplasia. When using this agent, the problems which arise in prostatic hyperplasia can be reduced.

From DE-OS 38 27 953, a pharmaceutical preparation is known consisting of an extract of the nettle root urtica kiovensis (Rogowicz), which comprises aromatic carboxylic-acids, phenols, lignans and phytosterols. The phytosterols contain primarily 13-sitosterin, campesterin, stigmasterin, and their oxidation products, 5,24(25)-stigmastadien-3-ol and stigmasta-4-en-3-on, apart from cholesterol.

For the treatment of prostatic hyperplasia or prostate carcinomas, it is suggested in DE-OS 34 01 178 that the 5(6)alpha-epoxycholesterol level should be reduced by the use of phytosterol glucosides and/or their esters.

From "Chemical Abstracts" 96(2):11546r, 99(12):93577a and 104(22):193257m, it is known that plant extracts from the bark of pygeum africanum may be used for the treatment of benign prostatic hyperplasia, and they contain 3-$\beta$-sitostenons together with a plurality of other active ingredients.

However, the disadvantage of all these known agents is that a relatively high quantity of the active ingredients must be used in order to obtain a reduction of the prostate volume and relief for the complaint.

Substances and agents are sought which permit the treatment of diseases which are influenced by androgenous hormones in comparatively small doses, and with which the side effects of therapy are reduced.

In particular, an active ingredient is sought for the treatment of benign prostatic hyperplasia.

Stigmasta-4-en-3-on is known as a substance and it constitutes an oxidation product of stigmasterol, a phytosterol.

According to JP 62-108899-Al, an oxidation product of stigmasterol, namely 24-stigmasta-4,24(28)-dien-3-one is used as an agent for growing hair. The use of stigmasta-4-en-3-one as a means for hair growth is also known from "Chemical Abstracts" 105(18):158615a and 106(4):23080x. Furthermore, U.S. Pat. No. 3,647,829 describes the hydration of stigmasta-4,22-dien-3-one when using palladium in the presence of tert-butylamine. A non-cosmetic, pharmaceutical use of the above dienone compound or its hydrated product is not known as yet.

The invention is based on the object of identifying active ingredients and pharmaceutical preparations which contain them, for successful use in the therapy of sexual hormone-dependant illnesses.

SUMMARY OF THE INVENTION

This problem is solved by a pharmaceutical preparation which comprises as the active ingredient stigmasta-4-en-3-one, optionally together with other pharmaceutical additive substances. Advantageous embodiments of the pharmaceutical prepartion in accordance with the invention include stigmasta-4-en-3-one in a pharmaceutical preparation with additive substances such as cellulose, lactose and maltodextrin. Preferably, the additive substance includes calcium carboxy methyl cellulose. Such a pharemaceutical preparation can be used in the treatement of testicular tumors, and especially benign prostatic hyperplasia.

Stigmasta-4-en-3-one has the formula below:

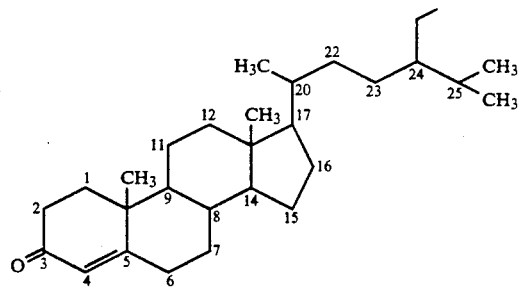

An additional double bond may also appear at the carbon atom 22, (stigmasta-4,22-dien-3-one) and the invention covers both variants.

According to the invention, it was discovered that stigmasta-4-en-3-one can be used with particularly good effect for the treatment of androgen-dependent diseases. A specially good effect was found when using this substance for the treatment of benign prostatic hyperplasia.

A significant reduction of the prostate weight was detected, and in comparison to plant extract pharmaceuticals which were previously used the concentration of the active ingredient can be substantially reduced.

DETAILED DESCRIPTION OF THE INVENTION

The pharmaceutical preparation in accordance with the invention contains stigmasta-4-en-3-one as the active substance, optionally with the addition of pharmaceutically acceptable additives. The usual additives can be considered, for example lactose or maltodextrin, with preference being given to lactose. Furthermore, cellulose preparations, particularly calcium carboxy methyl cellulose as well as talc and, in small amounts, magnesium stearate can be added. The pharmaceutical preparation according to the invention can be administered in the form of tablets, capsules or coated tablets, but it can also be administered intramuscularly, or subcutaneously in the form of an injection.

A preferred pharmaceutical preparation, which is administered in the form of tablets contains the following substances:

| | |
|---|---|
| stigmasta-4-en-3-on | 5 mg |
| lactose | 134 mg |
| calcium-carboxy methyl cellulose | 30 mg |
| Avicel ® (a cellulose preparation) | 10 mg |
| talc | 15 mg |
| magnesium stearate | 1 mg |

The content of stigmasta-4-en-3-on can be varied, preferably in a range from approximately 2 mg to about 20 mg. The above named substances are mixed in a ball mill and are then made up in the usual manner as tablets.

If the inventive pharmaceutical preparation is administered in the form of an injection, a solution is prepared and this solution of the active ingredient is e.g. either oily or diluted with alcohol. Preferably, ethanol is used as the alcohol.

The pharmaceutical preparations containing stigmasta-4-en-3-one ar useful in the treatment of androgen-dependant illnesses, for example in the treatment of testicular tumors, and especially benign prostatic hyperplasia. The pharmaceutical composition is administered to a subject suffering from, or likely to suffer from an androgen-dependant illness in an amount sufficient to have a therapeutic effect.

The daily dose of the active substance can be adjusted corresponding to the therapeutic requirement. An effective dose may be expediently within the range from about 20 to 80 mg/day, particularly 20 to 60 mg, but depending on the intensity of treatment, it can also be still more.

EXAMPLES

The invention will be explained in more detail below on the basis of some test results.

The anti-androgenous effect of Stigmasta-4-en-3-one was compared with that of a commercially available nettle root extract on animals. For the implementation of the test, fully-grown male rats, CO-breed (Sprague-Dawley, Charles River, Calco), having a weight of 280 to 300 g were kept in plastic boxes (26 ×42 ×16 cm) in air-conditioned rooms at constant temperature ($22° \pm 2°$ C.) and at relative humidity of $60 \pm 10\%$, as well as in artificial light (10 hours darkness; 10 hours light). Food and spring water were administered as required.

The anti-androgenous effect of the active substance according to the invention and of the known nettle root extract was analysed on the fully-grown rat, both in the absence as well as in the presence of increasing testosterone concentrations. For this purpose, the animals were gonadectomized and were given subcutaneous silastic implants (Dow Corning, Cat. No. 602-265, I.D.).

IMPLANT PREPARATION

The implants were filled with increasing testosterone concentrations (T), in order to achieve plasma testosterone values of between 0 and 2 ng/ml. The determination of plasma testosterone showed that implants which contained different testosterone concentrations (0 to 100%) and cholesterol (0 to 100%), released proportional amounts of testosterone, which remained constant for a certain period (4, 10 and 12 days). One percent implants were selected for this test, because they release testosterone amounts which are similar to those found in men who have prostate cancer, from whom the testicles were removed. Equally, 10%, 25% and 50% implants were chosen, because these testerone concentrations release testosterone amounts which are partly below, partly the same as, and partly more than those which are found in healthy males; in addition, information was obtained concerning the dose-effect relationship. Forty-eight hours before the operation, the implants were neutralized in NaCl (0.9%) at a temperature of 37° C. and the release of testosterone was measured in vitro every three hours for a period of 24 hours. Radioimmunoassay of testosterone in the medium showed that the steroid was released in concentrations which were both proportional as well as constant over a defined period.

OPERATION AND TREATMENTS

The animals were operated on at least three days after their arrival and acclimatization. The gonadectomy was carried out under slight ether narcosis and the implants were placed on the back, after an incision had been made.

For control, castrated and fully-grown male rats were investigated, on the one hand without testosterone concentrations and on the other, with increasing testosterone concentrations of 1%, 10%, 25 and 50%. None of the test substances were administered to these animals.

To investigate the effect of the active ingredient according to the invention, stigmasta-4-en-3-one, the test substance was administered in two different concentrations to the animals in addition to the above named implants with increasing testosterone concentrations. The concentrations of the active substance were 0.16 mg/kg body weight and 0.32 mg/kg body weight. Each test was carried out using the inventive active substance on 8 rats respectively.

For comparison, Bazoton (Kanoldt Arzneimittel GmbH), a commercially available nettle root extract was investigated, and implants with increasing testosterone concentrations were also used. The concentration of the nettle root extract obtainable on the market was 10 mg/kg body weight in one test, and 20 mg/kg body weight in a second test. When using this test substance as well, 8 rats were tested for each trial.

The administration of the test substance began on the date of the operation and was continued for 10 subsequent days. On the 11th day of treatment the animals were killed, 12 hours after the last administration. The substances were all administered intraperitoneally.

The animals were killed by decapitation. The blood was collected in test tubes containing heparin, centrifuged and the plasma was stored at −20° C. for determination of the plasma testosterone. The ventral prostates, the seminal vesicles and the adrenal glands were collected at 4° C., purified and stored for further analysis at −20° C.

The data were analysed using the Student-T-test.

The test substances were administered respectively in the form of a solution. The product available on the market consisting of a nettle root extract was administered chronically in an amount of 15 g with 1% NaCl gelatin (0.9%) in solution. The active substance in accordance with the invention, stigmasta-4-en-3-one, was administered chronically in an amount of 450 mg in a solution of ethanol and 1% NaCl gelatin (0.9%). The concentrations of both active substances were as stated above.

Of the 8 rats which were investigated, the body weight as well as the weight (in g) of the ventral prostate (expressed in mg) were respectively determined, both for the test without additional testosterone concentration, as well as for the tests with increasing testosterone concentration. Out of the eight values obtained, the average value was calculated in each case. The values thus obtained are shown in Table 1 below.

TABLE 1

| Active Substance | Body Weight (g) | Prostate Weight (mg) | | | | |
|---|---|---|---|---|---|---|
| | | 0% T | 1% T | 10% T | 25% T | 50% T |
| Control | 236.8 | 97.6 | 199.1 | 449.5 | 571.4 | 596.2 |
| Extract | | | | | | |
| 20 mg/kg | 307.5 | 103.1 | 145 | 290 | 308 | 403 |
| 10 mg/kg | 305.0 | 93.5 | 161.1 | 354 | 407 | 475.0 |
| S | | | | | | |
| 0.16 mg/kg | 295 | 91.3 | 173.1 | 360 | 425 | 507 |
| 0.32 mg/kg | 299.5 | 91.0 | 146.6 | 320.6 | 443 | 484 |

Control = No test substance
Extract = Nettle root extract
S = Stigmasta-4-en-3-one In the case of the control animals (without the test substance), the treatment using increasing testosterone doses induced a dose-dependent increase of the prostate weight, from 97.6 to 596.2 mg in doses of 0 to 50%.

The treatment with a nettle root extract obtainable on the market at dose of 20 mg/kg induced a reduction of the prostate weight beginning with the testosterone concentration of 1% up to a concentration of 50% with values which attained 145 to 403 mg after the implant of increasing testosterone doses. A corresponding dosing of 10 mg/kg induced a smaller inhibiting effect on the prostate weight, but in any case this achieved significance in doses of 10, 25 as well as 50% of testosterone.

The treatment using stigmasta-4-en-3-one reduced the weight of the ventral prostate significantly in both doses, i.e. 0.16 mg/kg and 0.32 mg/kg. It was found that the effect at the higher concentration was greater. In this case, good significance was achieved with a testosterone concentration of 1%.

A comparison of the test results thus obtained shows that when using the substance in accordance with the invention, substantially smaller amounts are necessary to attain an almost identical effect as a commercially available nettle-root extract.

While the prefered compositions and methods are illustrated in the foregoing description, many variations in materials and in the details of the illustrated method and composition will occur to those skilled in the art. It is intended that all such variations which fall within the scope and spirit of the appended claims be enbraced thereby.

We claim:

1. A method of treating an androgen-dependent cancer which comprises administering to a subject suffering therefrom or likely to suffer therefrom a therapeutically effective amount of stimasta-4-en-3-one.

2. A method of treating prostrate carcinoma and/or testicular tumors which comprises administering to a subject suffering therefrom or likely to suffer therefrom a therapeutically effective amount of stigmasta-4-en-3-one.

3. A method of treating benign prostate hyperplasia which comprises administering to a subject suffering therefrom or likely to suffer therefrom a therapeutically effective amount of stigmasta-4-en-3-one.

* * * * *